(12) United States Patent
Nakamura et al.

(10) Patent No.: US 9,919,990 B2
(45) Date of Patent: Mar. 20, 2018

(54) METHOD FOR MANUFACTURING METHYL FLUORIDE

(71) Applicant: DAIKIN INDUSTRIES, LTD., Osaka (JP)

(72) Inventors: Shingo Nakamura, Osaka (JP); Kanako Fukumoto, Osaka (JP); Yuusuke Etou, Osaka (JP); Tatsuya Ohtsuka, Osaka (JP); Masahiro Higashi, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 0 days.

(21) Appl. No.: 14/909,156

(22) PCT Filed: Aug. 7, 2014

(86) PCT No.: PCT/JP2014/070906
§ 371 (c)(1),
(2) Date: Feb. 1, 2016

(87) PCT Pub. No.: WO2015/020155
PCT Pub. Date: Feb. 12, 2015

(65) Prior Publication Data
US 2016/0168060 A1    Jun. 16, 2016

(30) Foreign Application Priority Data
Aug. 9, 2013    (JP) ................................ 2013-166919

(51) Int. Cl.
*C07C 17/093*    (2006.01)
*C07C 17/07*    (2006.01)
*C07C 17/361*    (2006.01)
*C07C 19/08*    (2006.01)

(52) U.S. Cl.
CPC ............ *C07C 17/361* (2013.01); *C07C 17/07* (2013.01); *C07C 17/093* (2013.01)

(58) Field of Classification Search
CPC ...... C07C 17/013; C07C 17/07; C07C 17/093
See application file for complete search history.

(56) References Cited

FOREIGN PATENT DOCUMENTS

| CN | 101633599 B | * | 11/2013 |
|----|----|----|----|
| JP | 62-501974 | | 8/1987 |
| JP | 4-7330 | | 2/1992 |
| JP | H0637399 B2 | * | 5/1994 |
| JP | 2006-111611 | | 4/2006 |
| JP | 2012-201666 | | 10/2012 |
| WO | 86/04893 | | 8/1986 |
| WO | 2011/102268 | | 8/2011 |

OTHER PUBLICATIONS

JPH0637399B2, May 5, 1994, pp. 1-7; English translation.*
Kim, D. E. et al. "New Method of Fluorination Using Potassium Fluoride in Ionic Liquid: Significantly Enhanced Reactivity of Fluoride and Improved Selectivity" J. Am. Chem. Soc. 2002, 124, pp. 10278-10279.*
Bram, G. et al. Synthetic Communications, 18(14), 1661-7; 1988 (Abstract and reaction details; pp. 1-2).*
Bram, G. et al. "Easy and Efficient Heterogeneous Nucleophilic Fluorination Without Solvent" Synthetic Communications, 18(14), 1661-1667 (1988).*
CN101633599B, Nov. 6, 2013, pp. 1-5 (Year: 2013).*
International Search Report dated Oct. 7, 2014 in corresponding International (PCT) Application No. PCT/JP2014/070906.
King, "Methyl Iodide", Organic Syntheses, Coll., vol. 2, 1943, pp. 399-406.

* cited by examiner

*Primary Examiner* — Medhanit W Bahta
(74) *Attorney, Agent, or Firm* — Wenderoth, Lind & Ponack, L.L.P.

(57) ABSTRACT

An object of the present invention is to provide a method for producing methane fluoride that is useful, for example, as a dry etching gas, the method being more suitable for industrial production. To achieve this object, the present invention provides a method including reacting (A) dimethyl sulfate and (B) at least one fluorocompound in a liquid phase, the fluorocompound (B) being at least one compound selected from the group consisting of hydrogen fluoride and hydrofluoric acid salts, or a metal fluoride, wherein when the fluoride compound (B) includes hydrogen fluoride or a hydrofluoric acid salt, the reaction is carried out without a solvent or using a polar solvent as a solvent, and when the fluoride compound (B) is a metal fluoride, the reaction is carried out using water as a solvent.

8 Claims, No Drawings

METHOD FOR MANUFACTURING METHYL FLUORIDE

TECHNICAL FIELD

The present invention relates to a method for producing methane fluoride, which is useful, for example, as a dry etching gas.

BACKGROUND ART

Hydrofluorocarbons are useful as an etching gas for the microfabrication of semiconductors, liquid crystals, etc. In particular, methane fluoride ($CH_3F$) has been attracting attention as an etching gas for forming state-of-the-art micro-structures.

For example, the following methods are known as methods for producing methane fluoride:
(1) a method comprising reacting methyl alcohol and hydrogen fluoride using a catalyst (PTL 1);
(2) a method comprising reacting methyl chloride and hydrogen fluoride using a catalyst (PTL 2);
(3) a method comprising pyrolyzing 1-methoxy-1,1,2,2-tetrafluoroethane (PTL 3); and
(4) a method comprising reacting dimethyl sulfate with an alkali metal fluoride, such as potassium fluoride, in the presence of a solvent having a polarity, such as diglyme or sulfolane, to produce monofluoromethane (PTL 4).

Among these methods, method (1) has the following disadvantages. The catalyst easily deteriorates due to the large amount of water generated. Manufacturing facilities easily corrode due to hydrofluoric acid produced as a result of the dissolution of unreacted hydrogen fluoride in the generated water.

Method (2) has the following problems. Because an excess of hydrogen fluoride must be added to improve the fluorination reactivity, the recycling and reuse of the hydrogen fluoride require large facilities and greatly increase the cost of manufacturing facilities. Furthermore, the introduction of moisture or the like as a contaminant may lower the reactivity and corrode the manufacturing facilities.

Further, method (3) requires cooling energy to separate methane fluoride (boiling point: −79° C.) from difluoroacetic acid fluoride, which is produced simultaneously with methane fluoride and which has a boiling point as low as 0° C. Furthermore, the resulting mixture contains a large amount of impurities, and separation of the impurities from methane fluoride is difficult even by rectification. In particular, among the impurities, trifluoromethane ($CHF_3$) has a boiling point of −84° C., which is close to the boiling point of methane fluoride, and is thus difficult to separate from methane fluoride. Furthermore, since the amount of trifluoromethane produced is associated with the starting material conversion, reducing the reaction conversion may be necessary to reduce the amount of trifluoromethane, which reduces production efficiency. Because the starting material 1-methoxy-1,1,2,2-tetrafluoroethane is synthesized by reacting tetrafluoroethylene and methanol, a risk of handling tetrafluoroethylene is also involved, and high costs of the starting materials and manufacturing facilities become a problem.

Lastly, method (4) requires a high-temperature reaction (about 150° C.) to obtain a sufficient amount of the product.

CITATION LIST

Patent Literature

PTL 1: JPH04-007330B
PTL 2: JP2006-111611A
PTL 3: WO2011/102268
PTL 4: JP2012-201666A

SUMMARY OF INVENTION

Technical Problem

In view of the above described state of the prior art, the present invention was made. A primary object of the invention is to provide a method for producing methane fluoride, the method being more suitable for industrial production. Specifically, a primary object of the present invention is to provide a method for safely and inexpensively producing methane fluoride with a high purity and a high yield by a low-temperature reaction without using a catalyst.

Solution to Problem

To achieve the above object, the present inventors carried out extensive research. As a result, the inventors found that when dimethyl sulfate and at least one specific fluorocompound, that is, hydrogen fluoride, a metal fluoride, and/or a hydrofluoric acid salt, are used as starting materials and when the presence or absence of a solvent and the type of solvent are selected according to the type of fluorocompound used, methane fluoride can be obtained with a high yield by a simple method comprising reacting the starting materials in a liquid phase without using a catalyst, the method producing few by-products that require a complicated separation procedure. Another advantage of this method is that because dimethyl sulfate and the fluorocompound to be used as starting materials are already used in methylation reactions, fluorination reactions, and the like widely performed, or as fluorination catalysts, these compounds are easily available at low cost. The present invention was accomplished as a result of further research based on these findings.

Specifically, the present invention includes the following.
Item 1. A method for producing methane fluoride ($CH_3F$), comprising reacting
(A) dimethyl sulfate and
(B) at least one fluorocompound in a liquid phase, the fluorocompound being at least one member selected from the group consisting of hydrogen fluoride and hydrofluoric acid salts, or a metal fluoride,
wherein when the fluorocompound (B) includes hydrogen fluoride or a hydrofluoric acid salt, the reaction is carried out without a solvent or using a polar solvent as a solvent, and when the fluorocompound (B) is a metal fluoride, the reaction is carried out using water as a solvent.
Item 2. The method according to Item 1, wherein the metal fluoride is at least one metal fluoride represented by formula (1):

$$MF \qquad (1)$$

(wherein M represents an alkali metal or an alkaline earth metal).
Item 3. The method according to Item 1 or 2, wherein the hydrofluoric acid salt is at least one hydrofluoric acid salt represented by formula (2) or (3):

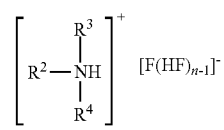

(2)

(wherein $R^2$, $R^3$, and $R^4$ are the same or different, and each represents hydrogen or an alkyl or cycloalkyl group that may be substituted with at least one halogen atom, and n is an integer of 1 to 5), or

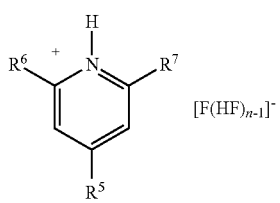

(3)

(wherein $R^5$, $R^6$, and $R^7$ may be the same or different, and each represents hydrogen or an alkyl or cycloalkyl group that may be substituted with at least one halogen atom, and n is an integer of 1 to 5).

Item 4. The method according to Item 3, wherein the hydrofluoric acid salt represented by formula (2) is ammonium fluoride ($NH_4F$), ammonium monohydrogen difluoride ($NH_4FHF$), methylamine fluoride ($CH_3NH_3F$), ethylamine fluoride ($C_2H_5NH_3F$), butylamine fluoride ($C_4H_9NH_3F$), dimethylamine fluoride (($CH_3)_2NH_2F$), diethylamine fluoride (($C_2H_5)_2NH_2F$), triethylamine fluoride (($C_2H_5)_3NHF$), or triethylamine trihydrofluoride (($C_2H_5)_3N.3HF$), and/or the hydrofluoric acid salt represented by formula (3) is a pyridine hydrofluoric acid salt.

Item 5. The method according to any one of Items 1 to 4, wherein the reaction is carried out without a solvent using hydrogen fluoride as the fluorocompound (B).

Item 6. The method according to Item 5, wherein the reaction is carried out using hydrogen fluoride in a state liquefied by pressure.

Item 7. The method according to any one of Items 1 to 4, wherein the reaction is carried out using a metal fluoride and/or a hydrofluoric acid salt as the fluorocompound (B) and using water as a solvent.

Item 8. The method according to Item 7, wherein the reaction is carried out by adding dimethyl sulfate (A) dropwise to an aqueous solution of the fluorocompound (B) in water.

Advantageous Effects of Invention

According to the present invention, methane fluoride can be obtained with a high starting material conversion and high selectivity by a simple method comprising subjecting inexpensive and easily available starting materials to a low-temperature liquid-phase reaction without using a catalyst, which is difficult to handle.

Furthermore, the methane fluoride obtained by the present invention is useful, for example, as a dry etching gas for forming a micro-structure in a semiconductor manufacturing process.

DESCRIPTION OF EMBODIMENTS

The production method according to the present invention is a process for producing methane fluoride ($CH_3F$), comprising reacting (A) dimethyl sulfate and (B) at least one fluorocompound in a liquid phase, the fluorocompound being at least one member selected from the group consisting of hydrogen fluoride and hydrofluoric acid salts, or a metal fluoride, wherein when the fluorocompound (B) includes hydrogen fluoride or a hydrofluoric acid salt, the reaction is carried out without a solvent or using a polar solvent as a solvent, and when the fluorocompound (B) is a metal fluoride, the reaction is carried out using water as a solvent. The production method of the present invention is described below in detail.

1. Fluorocompound (B)

The fluorocompounds (B) may be used singly or in a combination of two or more.

1.1 Metal Fluoride

The metal fluoride to be used is not particularly limited. Metal fluorides represented by formula (1) below are preferable.

$$MF \qquad (1)$$

(wherein M represents an alkali metal or an alkaline earth metal.)

Among the alkali metal fluorides represented by formula (1), lithium fluoride, sodium fluoride, potassium fluoride, rubidium fluoride, and cesium fluoride are preferable.

Among the alkaline earth metal fluorides represented by formula (1), magnesium fluoride, calcium fluoride, strontium fluoride, barium fluoride, and radium fluoride are preferable.

Among the metal fluorides represented by formula (1), lithium fluoride, sodium fluoride, potassium fluoride, and cesium fluoride are preferable. Potassium fluoride is more preferable.

1.2 Hydrofluoric Acid Salt

The hydrofluoric acid salt to be used is not particularly limited. Hydrofluoric acid salts (i) to (ii) below are preferable in view of the degree of conversion.

(i) Hydrofluoric Acid Salts Represented by Formula (2):

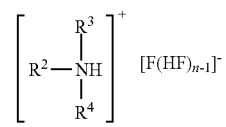

(2)

(wherein $R^2$, $R^3$, and $R^4$ are the same or different, and each represents hydrogen or an alkyl or cycloalkyl group that may be substituted with at least one halogen atom, and n is an integer of 1 to 5).

Among the above hydrofluoric acid salts, hydrofluoric acid salts of formula (2) wherein any of $R^2$, $R^3$, and $R^4$ is an alkyl or cycloalkyl group substituted with at least one halogen atom are preferably those wherein the substituent halogen atom is fluorine.

The hydrofluoric acid salt (i) is preferably a hydrofluoric acid salt represented by formula (2) wherein $R^2$, $R^3$, and $R^4$ are the same or different, and each represents hydrogen or a $C_{1-4}$ alkyl or $C_{3-6}$ cycloalkyl group that may be substituted with at least one halogen atom. Among such hydrofluoric acid salts, hydrofluoric acid salts of formula (2) wherein any of $R^2$, $R^3$, and $R^4$ is an alkyl or cycloalkyl group substituted with at least one halogen atom are preferably those wherein the substituent halogen atom is fluorine.

The hydrofluoric acid salt (i) is more preferably a hydrofluoric acid salt represented by formula (2) wherein $R^2$, $R^3$, and $R^4$ are the same or different, and each represents hydrogen, or a $C_1$ or $C_2$ alkyl or $C_3$ or $C_4$ cycloalkyl group that may be substituted with at least one halogen atom. Among such hydrofluoric acid salts, hydrofluoric acid salts of formula (2) wherein any of $R^2$, $R^3$, and $R^4$ are an alkyl or cycloalkyl group substituted with at least one halogen atom are preferably those wherein the substituent halogen atom is fluorine.

The hydrofluoric acid salt (i) is preferably a hydrofluoric acid salt represented by formula (2) wherein n is 1 to 5.

Preferred examples of the hydrofluoric acid salt (i) include ammonium fluoride ($NH_4F$), ammonium monohydrogen difluoride ($NH_4FHF$), methylamine fluoride ($CH_3NH_3F$), ethylamine fluoride ($C_2H_5NH_3F$), butylamine fluoride ($C_4H_9NH_3F$), dimethylamine fluoride (($CH_3)_2NH_2F$), diethylamine fluoride (($C_2H_5)_2NH_2F$), triethylamine fluoride (($C_2H_5)_3NHF$), and triethylamine trihydrofluoride (($C_2H_5)_3N.3HF$). Among these, ammonium fluoride ($NH_4F$), methylamine fluoride ($CH_3NH_3F$), ethylamine fluoride ($C_2H_5NH_3F$), and triethylamine trihydrofluoride (($C_2H_5)_3N.3HF$) are more preferable.

(ii) Hydrofluoric Acid Salts Represented by the Following Formula (3):

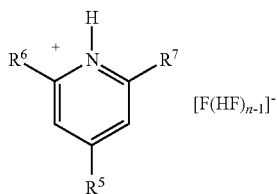

(wherein $R^5$, $R^6$, and $R^7$ are the same or different, and each represents hydrogen or an alkyl or cycloalkyl group that may be substituted with at least one hydrogen atom, and n is an integer of 1 to 5.)

Among the above hydrofluoric acid salts, hydrofluoric acid salts of formula (3) wherein any of $R^5$, $R^6$, and $R^7$ is an alkyl or cycloalkyl group that may be substituted with at least one halogen atom are preferably those wherein the substituent halogen atom is fluorine.

The hydrofluoric acid salt (ii) is preferably a hydrofluoric acid salt represented by formula (3) wherein n is 1 to 5.

The hydrofluoric acid salt (ii) is preferably a hydrofluoric acid salt represented by formula (3) wherein $R^5$, $R^6$, and $R^7$ are the same or different, and each represents hydrogen or a $C_{1-4}$ alkyl or $C_3$-6 cycloalkyl group that may be substituted with at least one halogen atom. Among such hydrofluoric acid salts, hydrofluoric acid salts of formula (3) wherein any of $R^5$, $R^6$, and $R^7$ is an alkyl or cycloalkyl group substituted with at least one halogen atom are preferably those wherein the substituent halogen atom is fluorine.

The hydrofluoric acid salt (ii) is more preferably a hydrofluoric acid salt represented by formula (3) wherein $R^5$, $R^6$, and $R^7$ are the same or different, and each represents hydrogen, or a $C_1$ or $C_2$ alkyl or $C_3$ or $C_4$ cycloalkyl group that may be substituted with at least one halogen atom. Among such hydrofluoric acid salts, hydrofluoric acid salts of formula (3) wherein any of $R^5$, $R^6$, and $R^7$ is an alkyl or cycloalkyl group that may be substituted with at least one fluorine atom are preferably those wherein the substituent halogen atom is fluorine.

Preferred examples of the hydrofluoric acid salt (ii) include pyridine hydrofluoric acid salts and the like.

When the fluorocompound (B) is a solid, the fluorocompound (B) is preferably in the form of particles as fine as possible. This is because finer particles can increase the surface area, and contact of the fluorocompound (B) with dimethyl sulfate (A) facilitates the progress of the reaction. For example, the potassium fluoride to be used preferably has a mean particle size of 10 to 50 μm, and more preferably a primary particle size of 0.1 to 5 μm. In particular, potassium fluoride is preferably in the form of fine particles having a specific surface area of at least 1 $m^2/g$ (BET method), and more preferably 1.5 $m^2/g$ or more. Such potassium fluoride can be produced, for example, by spray-drying to spray-dry the solution containing precipitates of potassium fluoride, although the method is not limited thereto.

Fluorides such as potassium fluoride, sodium fluoride, ammonium fluoride, and amine fluoride can be obtained by recycling a waste solution of fluoride generated by a neutralization treatment with potassium hydroxide, sodium hydroxide, aqueous ammonia, amine, or the like, in a process using hydrogen fluoride or a process generating hydrogen fluoride. Such a waste solution is heated or otherwise treated to evaporate water and thereby adjust the concentration, and the resulting product can be used as a starting material for the production method of the present invention.

2. Reaction Conditions

The reaction between dimethyl sulfate (A) and the fluorocompound (B) can proceed without a catalyst by bringing dimethyl sulfate (A) into contact with the fluorocompound (B) in a liquid phase directly or by using a solvent.

The reaction can proceed by adding the fluorocompound (B) to dimethyl sulfate (A), although the method is not limited thereto. In this case, the reaction can proceed, for example, by mixing the fluorocompound (B) into dimethyl sulfate (A) stored in a liquid state in a container and then heating while stirring, although the method is not limited thereto.

It is also possible to add dimethyl sulfate (A) to the fluorocompound (B) to allow the reaction to proceed, although the method is not limited thereto.

When the fluorocompound (B) includes hydrogen fluoride or a hydrofluoric acid salt, the reaction is carried out without a solvent or using a polar solvent as a solvent. When the fluorocompound (B) is a metal fluoride, the reaction is carried out using water as a solvent.

An aprotic solvent can be used as the polar solvent. Examples of the aprotic solvent include, but are not limited to, DMF and acetonitrile.

When an organic solvent is used, the organic solvent is preferably dried over a molecular sieve before use.

When water is used as a solvent, the reaction is preferably carried out at near neutrality in view of inhibiting the hydrolysis of dimethyl sulfate.

When water is used as a solvent, it is preferable that a mixture of the fluorocompound (B) with water is prepared beforehand and dimethyl sulfate is gradually added to the mixture. Although dimethyl sulfate (A) is hydrolyzed in aqueous solutions, the above method allows the desired reaction to proceed while minimizing the hydrolysis of dimethyl sulfate (A). An example of the method for gradually adding dimethyl sulfate is a method comprising adding liquid dimethyl sulfate dropwise while stirring a mixture of the fluorocompound (B) and water as needed. The dropping rate is not particularly limited and can be selected from a wide range usually used, such as 0.5 to 50 mL/h. In this case, stirring can be performed by using a magnetic stirrer or the like, although the method is not limited thereto.

When the reaction is carried out without a solvent using hydrogen fluoride as the fluorocompound (B), the desired methane fluoride is obtained in a particularly high yield. To allow hydrogen fluoride to react with dimethyl sulfate (A) without a solvent, the reaction is typically carried out using hydrogen fluoride in a state liquefied by pressure, although the method is not limited thereto. The pressure conditions are not particularly limited as long as hydrogen fluoride is pressurized into a liquid. For example, the pressure may be 0.1 to 1 MPa. In this case, the reaction is typically carried out using a pressure-resistant container.

When a fluoride metal salt and/or a hydrofluoric acid salt is used as the fluorocompound (B), the reaction is preferably carried out using water as a solvent. In this case, the desired methane fluoride can be obtained in an increased yield. In this case, as described above, it is preferable that a mixture of the fluorocompound (B) with water be prepared beforehand and dimethyl sulfate be gradually added to the mixture.

A reaction temperature that is too low tends to reduce the starting material conversion, whereas a reaction temperature that is too high tends to increase impurities. In view of these problems, although it also depends on the presence or absence of a solvent and the type of solvent used, when water is used as a solvent, the reaction temperature is preferably 50° C. to 150° C., more preferably 80° C. to 120° C., and even more preferably 90° C. to 110° C. When a polar solvent is used as a solvent, the reaction temperature is preferably 70° C. to 300° C., more preferably 80° C. to 200° C., and even more preferably 100° C. to 120° C. When no solvent is used, the reaction temperature is preferably 80° C. to 200° C., more preferably 100° C. to 180° C., and even more preferably 100° C. to 150° C.

The method of the present invention is advantageous in that it allows the reaction to proceed at a temperature lower than the temperatures used in conventional methods, such as lower than 150° C., not higher than 120° C., or not higher than 100° C. According to the present invention, a sufficient amount of the product can be obtained at temperatures at which a sufficient amount of the product is difficult to obtain by using conventional methods.

A pressure that is too low during the reaction may result in the introduction of air, which requires a complicated procedure. In contrast, a pressure that is too high requires the pressure resistance of the equipment to be taken into consideration and increases the risk of leakage. From these viewpoints, a reaction pressure with no need for pressurization is preferably 0.05 to 1 MPa, and more preferably 0.1 to 0.5 MPa. In particular, in view of the ease of the reaction procedure, the pressure is preferably at an atmospheric pressure level (about 0.1 MPa).

The reaction time is not particularly limited. When the time of contact between the starting materials is too long, it takes a long time to obtain the product. Accordingly, a shorter contact time is preferable to increase the amount of production. However, an excessively short contact time tends to reduce the conversion. Therefore, the contact time that provides the highest productivity in view of the starting material conversion and selectivity of the desired product should be selected according to the reaction conditions.

In the production method of the present invention, using a catalyst is not particularly necessary. Catalysts may be used as needed.

The molar ratio of the fluorocompound (B) to dimethyl sulfate (A) is preferably as large as possible. However, because a high molar ratio of the fluorocompound (B) increases the manufacturing cost, the fluorocompound (B) is preferably used in excess within an economically acceptable range. For example, the molar ratio of the fluorocompound (B) to dimethyl sulfate (A) is preferably in the range of 1 to 100, more preferably from 5 to 50, and even more preferably from 20 to 50.

The methane fluoride obtained by the method of the present invention can be separated and purified by a known method, as needed. For example, distillation or extraction can be used for purification.

The methane fluoride obtained by the method of the present invention is useful, for example, as a dry etching gas for forming a micro-structure in a semiconductor manufacturing process.

EXAMPLES

The present invention is described below in more detail with reference to Examples.

1. Examples 1 to 5

1.1 Example 1

After 12 g (0.21 mol) of potassium fluoride and 25 g of pure water were placed in a 100-cc pressure-resistant container, 10 g (0.08 mol) of dimethyl sulfate was added to start the reaction. After the temperature had reached 100° C., the reaction was allowed to proceed for 5 hours. The final pressure was 0.15 MPa/G. The generated gas was collected and analyzed by gas chromatography. With the theoretical yield of methane fluoride obtained by this reaction being assumed to be 0.08 mol, the yield of methane fluoride was calculated and found to be 0.08 mol. The yield was 100%.

1.2 Example 2

After 10 g (0.17 mol) of potassium fluoride and 20 mL of acetonitril were placed in a 100-cc pressure-resistant container, 10 g (0.08 mol) of dimethyl sulfate was added to start the reaction. The reaction was allowed to proceed at 100° C. for 4 hours. The gas generated was collected and analyzed by gas chromatography. With the theoretical yield of methane fluoride obtained by this reaction being assumed to be 0.08 mol, the yield of methane fluoride was calculated and found to be 27%. The selectivity of methane fluoride in the generated gas was 71%. As impurities, 21% of dimethyl ether and 8% of methyl formate were detected.

1.3 Example 3

After 10 g (0.08 mol) of dimethyl sulfate was placed into a 100-cc pressure-resistant container, 10 g (0.5 mol) of hydrogen fluoride was added to start the reaction. The reaction was allowed to proceed at a temperature of 50° C. and a pressure of 0.15 MPa/G for 5 hours. The gas generated was collected and analyzed by gas chromatography. With the theoretical yield of methane fluoride obtained by this reaction being assumed to be 0.16 mol, the yield of methane fluoride was calculated and found to be 53%. The selectivity of methane fluoride in the generated gas was 53%. As impurities, 41% of methane and 6% of ethane were detected.

2. Examples 4 to 11

After potassium fluoride (KF), water, and a magnetic stirrer were placed in a two-necked round bottomed flask (35 mL) equipped with an Allihn condenser and a dimethyl sulfate (DMS) feeder, the system was closed. A Tedlar bag for collecting the generated gas was previously mounted to the tip of the Allihn condenser so as to prevent the pressure inside the system from exceeding atmospheric pressure. With water flowing through the Allihn condenser for cooling, the aqueous potassium fluoride solution was heated to a reaction temperature in an oil bath while stirring the solution. When the reaction temperature was reached, dimethyl sulfate was added dropwise using the dimethyl sulfate (DMS) feeder.

After HFC-32 was added as an internal standard to the gas collected in the Tedlar bag, HFC-41 was quantified by gas chromatography equipped with a GS-GASPRO column. The residual liquid in the flask was diluted with water. After $CH_3COONa$ was added as an internal standard, 1H NMR ($D_2O$) was measured and the conversion of dimethyl sulfate was calculated.

Table 1 shows the results of Examples 4 to 11.

TABLE 1

| Example | KF aqueous solution | | | DMS | | Molar ratio KF/DMS | Reaction | | DMS Conversion (%) | HFC-41 Yield (%) |
| | KF (g) | Water (ml) | Concentration (%) | Drop volume (g) | Dropping rate (mL/h) | | Temperature (° C.) | Time (h) | | |
|---|---|---|---|---|---|---|---|---|---|---|
| 4  | 5.8 | 9  | 64  | 13  | 20  | 1  | 100 | 3.5 | 100 | 27 |
| 5  | 25  | 25 | 100 | 10  | 7.5 | 5  | 100 | 3   | 100 | 24 |
| 6  | 25  | 25 | 100 | 2.5 | 4.0 | 22 | 100 | 2   | 100 | 66 |
| 7  | 21  | 21 | 100 | 2.0 | 1.0 | 22 | 60  | 4   | 100 | 57 |
| 8  | 21  | 21 | 100 | 2.0 | 1.0 | 22 | 115 | 2   | 100 | 69 |
| 9  | 4.6 | 10 | 46  | 2.0 | 4.0 | 5  | 100 | 1   | 100 | 32 |
| 10 | 21  | 21 | 100 | 2.0 | 1.0 | 22 | 100 | 2   | 100 | 68 |
| 11 | 40  | 20 | 200 | 1.9 | 1.0 | 46 | 100 | 2   | 100 | 80 |

The main impurity was methanol, and 12% or less of dimethyl ether and 0.1% or less of dimethoxymethane were detected.

A conversion of 100% was achieved over the entire dropping rate range of 1 to 20 mL/h (Example 4).

The results also show that a higher temperature tends to provide a higher yield (Examples 7, 10, and 8).

Further, the results show that a higher molar ratio (KF/DMS) tends to provide a higher yield (Examples 6 and 9 and Examples 10 and 11). A molar ratio (KF/DMS) of 46 provided a yield of 80%.

3. Comparative Example 1

The reaction was allowed to proceed under the same conditions as in Example 2 except that the reaction temperature was set to 60° C. Little methane fluoride was obtained.

4. Comparative Example 2

To make a comparison with Examples 4 to 11 using water as a solvent, a reaction was carried out in a similar manner using diglyme as a solvent. The reaction conditions are shown in Table 2.

Table 2 shows the results. The yield was 1.5%. It is thought that since only a small amount of KF was dissolved in the solvent, the reaction did not proceed.

5. Example 12

$Et_2N.3HF$ (2.02 g, 12.5 mmol) and $Me_2SO_4$ (1.58 g, 12.5 mmol) were placed in a glass 50-mL round bottomed flask equipped with an Allihn condenser and a Tedlar bag. The reaction was allowed to proceed at 140° C. for 5 hours. The amount of gas collected in the Tedlar bag was 0.33 g. The selectivity of $CH_3F$ in the generated gas was 100%. With the theoretical yield of methane fluoride obtained by this reaction being assumed to be 12.5 mmol, the yield of methane fluoride was calculated. The yield of methane fluoride was 77%.

6. Example 13

$Et_3N.3HF$ (4.03 g, 25 mmol) and $Me_2SO_4$ (3.15 g, 25 mmol) were placed in a glass 50-mL round bottomed flask equipped with an Allihn condenser and a Tedlar bag. The reaction was allowed to proceed at 100° C. for 5 hours. The amount of gas collected in the Tedlar bag was 0.55 g. The selectivity of $CH_3F$ in the generated gas was 100%. With the theoretical yield of methane fluoride being assumed to be 25 mmol, the yield of methane fluoride was calculated. The yield of methane fluoride was 65%.

As described above, in Examples 12 and 13, methane fluoride was obtained with high efficiency at a low temperature of 140° C. or less at atmospheric pressure in a glass container.

The invention claimed is:
1. A method for producing methane fluoride ($CH_3F$) comprising reacting
   (A) dimethyl sulfate and
   (B) at least one fluorocompound in a liquid phase, the fluorocompound being a metal fluoride or at least one member selected from the group consisting of hydrogen fluoride and hydrofluoric acid salts,

TABLE 2

| Comparative Example | KF solution | | | DMS | | Molar ratio KF/DMS | Reaction | | DMS Conversion (%) | HFC-41 Yield (%) |
| | KF (g) | Diglyme (mL) | Concentration (%) | Drop volume (g) | Dropping rate (mL/h) | | Temperature (° C.) | Time (h) | | |
|---|---|---|---|---|---|---|---|---|---|---|
| 2 | 20 | 20 | Saturated | 2 | 1 | 15 | 100 | 6 | 7.9 | 1.5 | wherein:

the molar ratio of the fluorocompound (B) to dimethyl sulfate (A) is from 22 to 50, and when the fluorocompound (B) is a metal fluoride, the reaction is carried out using a solvent consisting of water, and when the fluorocompound (B) includes hydrogen fluoride or a hydrofluoric acid salt, the reaction is carried out without a solvent or using a solvent consisting of water, wherein when the solvent consisting of water is used, a mixture of the fluorocompound (B) with the solvent consisting of water is prepared and then dimethyl sulfate (A) is gradually added to the mixture at 0.5 to 50 mL/h.

2. The method according to claim 1, wherein the metal fluoride is at least one metal fluoride of formula (1):

MF     (1)

wherein M represents an alkali metal or an alkaline earth metal.

3. The method according to claim 1, wherein the hydrofluoric acid salt is at least one hydrofluoric acid salt of formula (2) or (3):

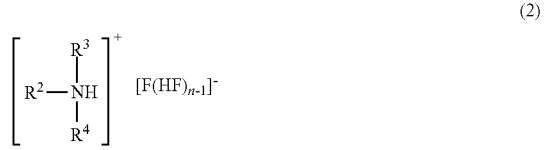

(2)

wherein $R^2$, $R^3$, and $R^4$ are the same or different and each represents hydrogen or an alkyl or cycloalkyl group that may be substituted with at least one halogen atom, and n is an integer of 1 to 5, or

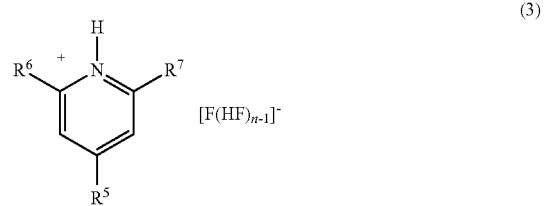

(3)

wherein $R^5$, $R^6$, and $R^7$ may be the same or different, and each represents hydrogen or an alkyl or cycloalkyl group that may be substituted with at least one halogen atom, and n is an integer of 1 to 5.

4. The method according to claim 3, wherein the hydrofluoric acid salt of formula (2) is ammonium fluoride ($NH_4F$), ammonium hydrogen difluoride ($NH_4FHF$), methylamine fluoride ($CH_3NH_3F$), ethylamine fluoride ($C_2H_5NH_3F$), butylamine fluoride ($C_4H_9NH_3F$), dimethylamine fluoride (($CH_3)_2NH_2F$), diethylamine fluoride (($C_2H_5)_2NH_2F$), triethylamine fluoride (($C_2H_5)_3NHF$), or triethylamine trihydrofluoride (($C_2H_5)_3N.3HF$), and/or the hydrofluoric acid salt of formula (3) is a pyridine hydrofluoric acid salt.

5. The method according to claim 1, wherein the reaction is carried out without a solvent using hydrogen fluoride as the fluorocompound (B).

6. The method according to claim 5, wherein the reaction is carried out using hydrogen fluoride in a state liquefied by pressure.

7. The method according to claim 1, wherein the reaction is carried out using a metal fluoride and/or a hydrofluoric acid salt as the fluorocompound (B) and using a solvent consisting of water.

8. The method according to claim 7, wherein the reaction is carried out by adding dimethyl sulfate (A) dropwise to an aqueous solution of the fluorocompound (B) in water.

* * * * *